(12) United States Patent
Mitter et al.

(10) Patent No.: US 6,483,324 B1
(45) Date of Patent: Nov. 19, 2002

(54) SYSTEM FOR MEASURING HUMIDITY

(75) Inventors: Helmut Mitter, Hellmonsodt; Dieter Wagner; Josef Hartl, both of Linz, all of (AT)

(73) Assignee: E & E Elektronik Ges. m.b.H., Engerwitzdord (AT)

( * ) Notice: Subject to any disclaimer, the term of this patent is extended or adjusted under 35 U.S.C. 154(b) by 0 days.

(21) Appl. No.: 09/582,856
(22) PCT Filed: Oct. 28, 1999
(86) PCT No.: PCT/EP99/08165
§ 371 (c)(1),
(2), (4) Date: Aug. 21, 2000
(87) PCT Pub. No.: WO00/28311
PCT Pub. Date: May 18, 2002

(30) Foreign Application Priority Data

Nov. 6, 1998 (AT) .................................. 724/98

(51) Int. Cl.$^7$ .............................................. G01R 27/08
(52) U.S. Cl. .................... 324/689; 324/696; 73/335.03; 73/335.05
(58) Field of Search ................................. 324/696, 689, 324/694, 663, 664; 73/335.03, 335.05

(56) References Cited

U.S. PATENT DOCUMENTS

| | | | | |
|---|---|---|---|---|
| 3,848,218 A | * | 11/1974 | Wakabayashi et al. ........ 338/35 |
| 3,914,982 A | | 10/1975 | Zanetti | |
| 3,983,527 A | * | 9/1976 | Ohsato et al. ................. 338/35 |
| 4,337,658 A | * | 7/1982 | Motchenbacher et al. ....................... 73/335.03 |
| 4,562,725 A | * | 1/1986 | Oka et al. .................... 73/29.05 |
| 4,603,455 A | * | 8/1986 | Woest et al. ................ 29/25.42 |
| 4,642,601 A | * | 2/1987 | Sugawara et al. ............. 338/35 |
| 4,942,364 A | * | 7/1990 | Nishijima et al. ........... 324/696 |
| 5,179,347 A | * | 1/1993 | Hawkins ..................... 324/696 |
| 5,345,821 A | | 9/1994 | Reich et al. | |
| 5,388,443 A | | 2/1995 | Manaka | |

FOREIGN PATENT DOCUMENTS

| | | |
|---|---|---|
| DE | 39 24 634 | 1/1991 |
| JP | 61 235745 | 10/1986 |
| WO | WO 98/27411 | 6/1998 |

OTHER PUBLICATIONS

H.R. Trankler et al., "Sensor Technik" Chapter 20.4, pp. 1245–1250, 1998, No month available.
H. R. Trankler et al., "Sensor Technik" Chapter 6.6.22, pp. 277–278, 1998 No month available.

* cited by examiner

Primary Examiner—N. Le
Assistant Examiner—Vincent Q. Nguyen
(74) Attorney, Agent, or Firm—Kenyon & Kenyon

(57) ABSTRACT

A device for measuring moisture is described. This device includes a sensor unit (1) having a moisture-sensitive sensor element (1.1) and a carrier element (2), upon which the sensor unit is mounted. The carrier element (2), as well as the sensor unit (1) have electrical contact regions (1.2a, 1.2b). Carrier element (2) has a recess (6), above which the sensor unit (1) is mounted. The moisture-sensitive sensor element (1.1) is oriented in the direction of the recess (6). The sensor-side contact regions are formed on the side of the sensor unit (1) facing the carrier element (2). In at least one partial region adjacent to the sensor unit (1), the carrier element (2) is provided with a coating (3) which absorbs and/or releases as little moisture as possible.

33 Claims, 3 Drawing Sheets

SYSTEM FOR MEASURING HUMIDITY

The present invention relates to a device for measuring moisture, and more specifically to a device for measuring moisture in which the measurement is not affected by the arrangement of the device.

DESCRIPTION OF THE RELATED ARTS

Devices for measuring moisture are known, where a sensor unit having a moisture-sensitive sensor element is mounted on a flat carrier element. The carrier element can be, for example, a circuit board or a wafer. In this case, the required electrical contacts between electrical components mounted on the circuit board, for generating and processing signals, and the sensor unit or the actual moisture-sensitive sensor element, can be provided by bonding wires and corresponding soldered connections.

Alternatively, the contact can also be carried out via connection wires at the sensor unit, which are inserted into suitable contact bores on the carrier element side, and are soldered on the other side to the circuit board. However, from a standpoint of production engineering, use of contact elements of this kind requires substantial expense, which is especially perceived as being negative in the case of mass production. The automated fitting of circuit boards with sensor units of this kind for measuring moisture is difficult or even impossible using these types of contacts.

From WO 98/27411, a locally selective system is known, where, for example, a sensor in the form of a moisture sensor is configured with its moisture-sensitive sensor surface above the recess of a suitable carrier substrate. Flip-chip technology is used for the electrical contacting of the sensor element. However, this device can have the drawback of measured moisture values being invalidated when certain carrier substrate materials are used.

SUMMARY OF THE INVENTION

The present invention is a device for measuring moisture, which renders possible a substantially automated manufacture of such devices. The device requires a simplest possible electrical contacting of the components used. In addition, with the present invention, the measured moisture values are not invalidated by the design of the device.

The systems according to the present invention now permit the automatic fitting of circuit boards, wafers, or other carrier elements with moisture-sensitive sensor units. The sensor units can be, for example, SMDs (surface mounted devices). In this case, the sensor units are placed in an automated fashion, by SMD automatic insertion equipment, at the designated positions of the carrier elements designed in accordance with the present invention, secured in place, and electrically contacted. The complete or simultaneous contacting of the sensor unit can be achieved, for example, by hard-soldering, or it can also be achieved by fastening with conductive gel. In comparison to the conventional method of contacting and fitting, the result is a clear reduction in the required process steps due to the now possible flip-chip technology.

In addition, the embodiments of the invention, ensure a trouble-free functioning of the device during the measuring operation, since it is possible to prevent a microclimate from developing in the vicinity of the sensor unit and affecting the measurements.

In one embodiment, the invention is thus a device for measuring moisture, comprising a sensor unit with a moisture-sensitive sensor element, a carrier element defining a recess, wherein the sensor unit is mounted above the recess, and the moisture-sensitive sensor element is oriented in the direction of the recess. The invention also includes first electrical contact regions of the carrier element, second electrical contact regions of the sensor unit, the second electrical contact regions being disposed on the sensor unit facing the carrier element, and a moisture absorption and desorption resistant coating disposed on the carrier element at least in one partial region adjacent to the sensor unit.

Within the scope of the present invention, the most widely varying designs are possible for particular moisture-sensitive sensor units, since the measures described in the following can be adapted to very different circumstances. For example, both capacitive variants, as well as resistive variants of a moisture-measuring device can be implemented in accordance with the present invention.

BRIEF DESCRIPTION OF THE DRAWINGS

Further advantages, as well as details pertaining to the device according to the present invention are disclosed in the following description of an exemplary embodiment, with reference to the enclosed drawings.

In the Drawings.

DETAILED DESCRIPTION OF THE EMBODIMENTS OF THE INVENTION

Figure 1:
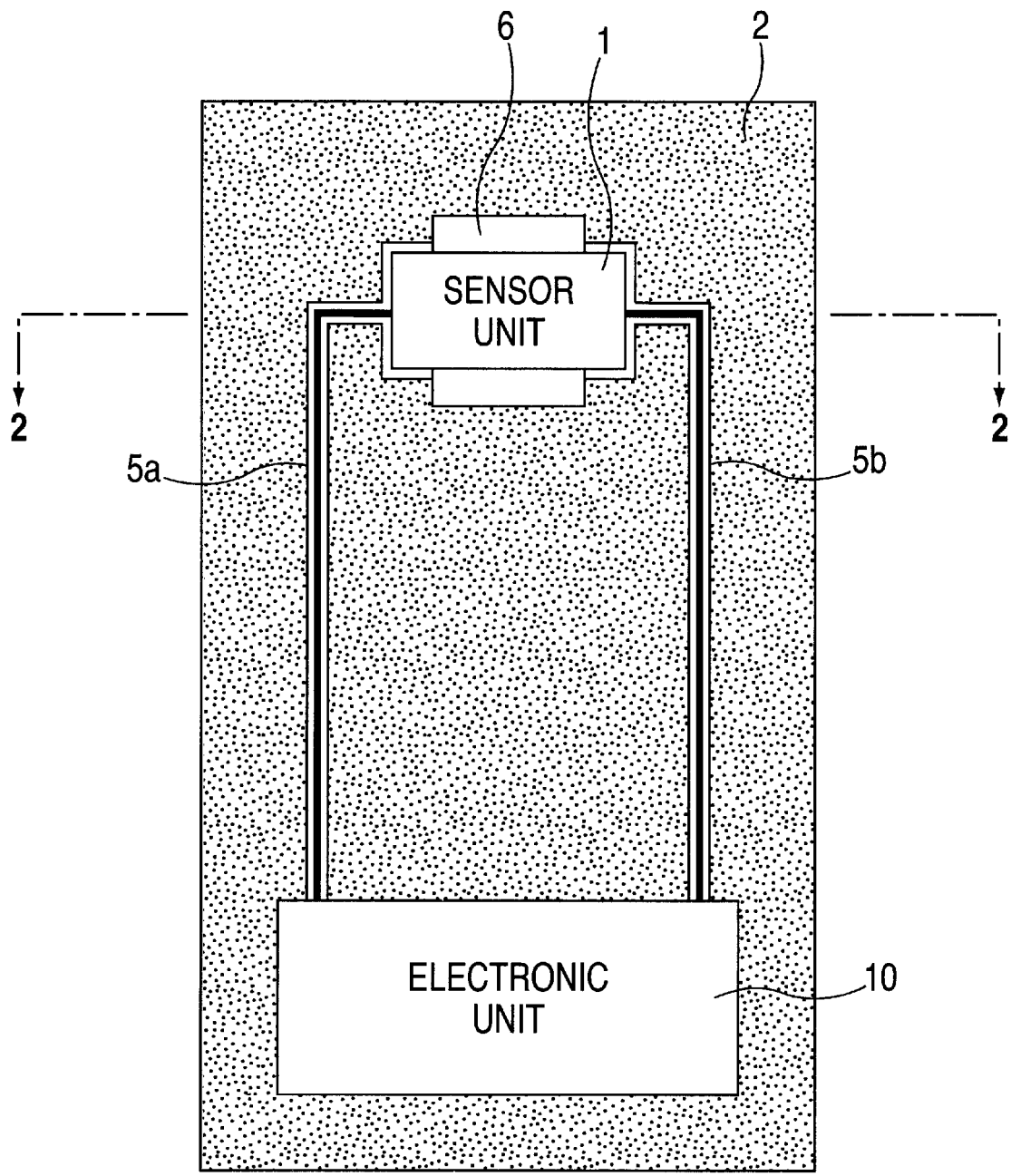
FIG. 1 is a plan view of an exemplary embodiment of the device according to the present invention.
Figure 2:
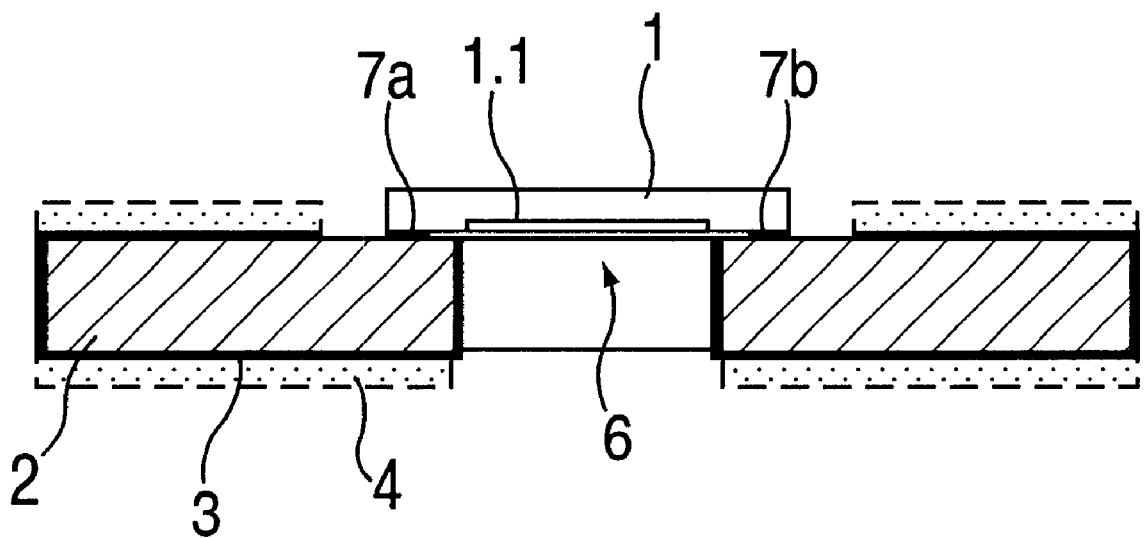
FIG. 2 is a sectional view of the exemplary embodiment according to FIG. 1.

FIGS. 1 and 2 illustrate an exemplary embodiment of the device in accordance with the present invention, as described in the following. A plan view of the device for measuring moisture is schematically depicted in FIG. 1, and FIG. 2 illustrates a sectional view through the device. The depicted device includes a carrier element 2, which is preferably a single- or multi-layer circuit board having electrical printed conductors 5a, 5b, and other electrical components arranged thereon or integrated therein. The circuit board material can be, for example, glass fiber-reinforced epoxy resin, such as the known standard circuit board material FR4.

Placed on carrier element 2, using the so-called flip-chip technique, there is a sensor unit 1 which can comprise a moisture-sensitive sensor element 1.1. Sensor element 1.1 is designed in a well known fashion and possesses characteristic electrical properties that change as a function of the prevailing moisture. In the case of a resistive moisture sensor device, the moisture-dependent electrical resistance of a suitable sensor element 1.1 varies. In the case of a capacitive moisture sensor device, the measured capacitance of a corresponding sensor element 1.1 varies as a function of the moisture.

Sensor element 1.1 in sensor unit 1 can be preferably designed, in this case, as a thin layer or thin-layer sensor, as described for example, in "Sensortechnik" (Sensor Technology), Chapter 20.4, pages 1245–1250, H. R. Tränkler, E. Obermeier, Springer Publishers 1998.

Further details of a preferred exemplary embodiment of sensor unit 1 and of sensor element 1.1, are described with reference to the following figures. In FIG. 2, a sketch of the design of sensor unit 1 is presented. Moisture-sensitive sensor element 1.1 can be disposed on the bottom side of sensor unit 1, i.e., on that side of sensor unit 1 facing carrier element 2. To ensure that moisture-sensitive sensor element 1.1 is able to interact with the prevailing ambient environment, such that the ambient moisture effects a change in the capacitance in sensor element 1.1, the present invention provides for carrier element 2 to have at least one recess 6 in the area where sensor unit 1 is mounted. Sensor unit 1 can be disposed above recess 6, with moisture-sensitive sensor element 1.1 of sensor unit 1 being oriented in the direction of recess 6. In the case where a sensor element 1.1 is a thin-layer which acts as a dielectric material in a capacitive measuring device, the layer surface faces recess 6. This can preferably be achieved by arranging the plane of the layer in recess 6, or parallel to and adjacent to the plane of recess 6.

Other variants of the device according to the invention can be made. In all the embodiments, the moisture-sensitive sensor element should be arranged relative to the recess in a manner that permits moisture exchange between the sensor element and the ambient environment, in the most undisturbed possible fashion.

In the depicted exemplary embodiment, recess 6 is selected to be larger than the corresponding surface area of sensor unit 1 or of sensor element 1.1, which faces carrier element 2. As a result, the complete sensor unit 1 is advantageously circumflowed by the air to be measured and, thus, an improved moisture exchange with sensor element 1.1 is achieved.

To ensure the requisite electrical contacting of sensor unit 1 and of moisture-sensitive sensor element 1.1, the preferred embodiment according to the present invention includes placing all contacting regions or contact pads of sensor element 1.1 or of sensor unit 1 on the side which faces carrier element 2. This enables a flip-chip bonding of sensor unit 1 onto carrier element 2. For further details and advantages of this contacting technique, reference is made, for example, to "Sensortechnik" (Sensor Technology), chapter 6.6.2.2, pages 277–278, H.-R. Tränkler, E. Obermeier, Springer Publishers 1998.

Accordingly, in the depicted exemplary embodiment of FIGS. 1 and 2, the contact regions or contact pads of sensor element 1.1 are arranged on the bottom side of sensor unit 1. The contact regions of sensor element 1.1 are electro conductively connected with the aid of contacting elements 7a, 7b to the contact regions on carrier element 2.

Various options exist to obtain the selected electrical contacting. In one preferred specific embodiment, the contact elements can be applied in the form of a suitable soldering paste to the contact regions of carrier element 2. Sensor unit 1 is subsequently positioned at the correct location on carrier element 2. The actual contacting then follows, in a generally known manner, by tempering the entire arrangement in the reflow oven.

Alternatively, in the case of contacting elements 7a, 7b between the sensor- and carrier-side contact regions, the located contacts can also be obtained using "bumps", or build-ups composed of electrically conductive solder material or of conductive gel. Besides providing the electrical connection, contacting elements 7a, 7b also ensure that sensor unit 1 is securely attached to carrier element 2.

Figure 3:
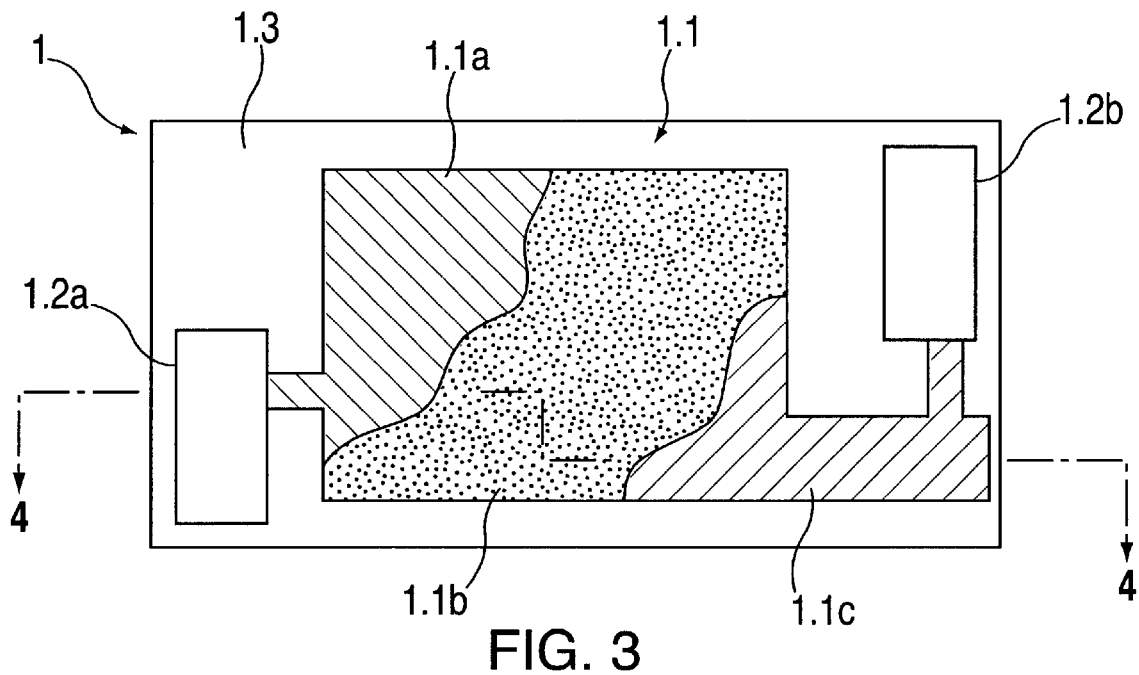
FIG. 3 is a plan view of the moisture-sensitive sensor element used in the exemplary embodiment of FIG. 1.
Figure 4:
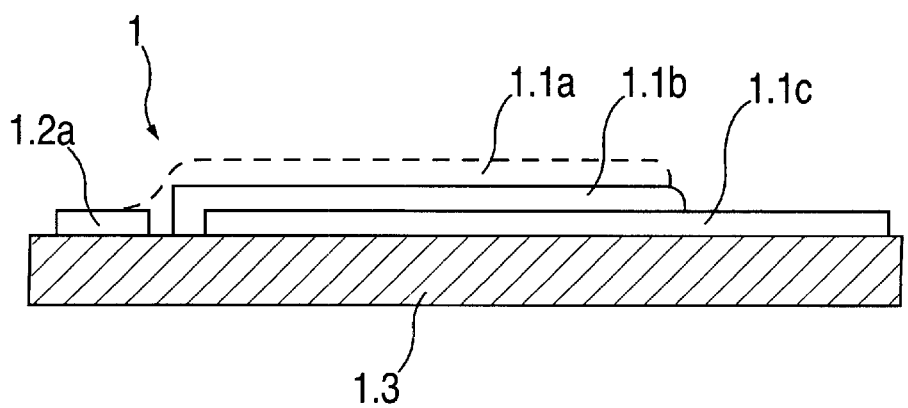
FIG. 4 is a sectional view of the sensor element of FIG. 3.

Accordingly, in this manner, the two electrodes of a capacitive moisture-measuring arrangement are electro conductively connected. Between the two electrodes, there is the sensor element 1.1, formed by an active layer whose capacitance varies as a function of moisture, in response to water absorption. A detailed design of an exemplary embodiment of sensor unit 1 is shown in FIGS. 3 and 4.

The contact regions provided on carrier element 2, in turn, are connected to two printed conductors 5a, 5b, which connect sensor unit 1 to a schematically indicated electronic unit 10. Electronic unit 10 can contain further electrical components for producing and/or processing signals. These can be, for example, resistors, capacitors, comparators, operational amplifiers, as well as, if indicated, microprocessors.

When measuring moisture with the aid of sensor unit 1 on carrier element 2, a number of further measures can be taken to ensure that measured values are not invalidated due to the carrier element material selected. These measures are to be resorted to, in particular, when the material selected for carrier element 2 has a strong moisture absorption or desorption characteristics. If these measures are not taken, in the case of circuit board material FR4, a microclimate can develop in the ambient environment of sensor unit 1, which can lead to erroneous measurements.

In the depicted exemplary embodiment of the arrangement according to the present invention, carrier element 2 has a virtually complete coating 3. For this purpose, carrier element 2 or the circuit board are provided, substantially over their entire surface, with a coating 3 of copper. In this case, as shown in FIG. 2, coating 3 is also provided at the rims or edges of carrier element 2. Similarly, the inner rims of recess 6 can be provided with coating 3 in the area of recess 6 where sensor element 1.1 is located.

At least in the immediate area surrounding sensor unit 1, carrier element 2 should be nearly completely coated in this manner using a suitable coating material, in order to prevent a falsifying microclimate from developing there. The coating material in question essentially has the function of preventing unwanted moisture absorption and/or desorption through the carrier element material in question. The coating material 3 should therefore be an absorption and desorption resistant material.

Alternatively or in addition to copper, other materials can also be used as coating material. Thus, in addition to or alternatively to a copper coating, a nickel coating, a gold coating or a tin coating could also be provided.

In a preferred embodiment, coating 3 is not applied in the area of the contacting regions of carrier element 2, where contacting elements 7a, 7b are arranged, as is indicated in FIG. 2. The coating is thus only applied to non-contact region surfaces of carrier element 2. Furthermore, as is shown in FIG. 1, no coating is provided directly adjacent to printed conductors 5a, 5b on carrier element 2, to insulate printed conductors 5a, 5b from the copper coating. In one advantageous specific embodiment, the printed conductors are also made of copper, or of whichever particular coating material is used, so that once carrier element 2 is coated over its entire surface with copper, suitable patterning measures can be used to produce the required printed conductors. A generally known etching process can be used for this process.

As is furthermore discernible from the sectional view in FIG. 2, coating 3 of carrier element 2 can additionally be provided, virtually over its entire surface, with another, second coating 4 in the form of a solder resist. However, in the contacting regions of carrier element 2, where sensor unit 1 is electrically connected, a second coating 4 is not provided. In selecting a suitable solder resist, a material is selected having the lowest possible characteristics of moisture absorption and desorption, so that a disturbing microclimate which can invalidate the measured values cannot develop in the vicinity of sensor unit 1. Particularly suited for this use are, for example, solder resists which absorb less than 2% moisture.

FIGS. 3 and 4 illustrate sensor unit 1 of the exemplary embodiment. FIG. 3 illustrates the bottom side of sensor unit 1, which faces carrier element 2. FIG. 4 shows a detailed sectional representation through the sensor unit 1. In the depicted exemplary embodiment, sensor unit 1 includes a capacitive measuring arrangement, having a carrier substrate 1.3 of glass, on which are arranged the actual moisturesensitive sensor element 1.1, as well as contacting regions 1.2a, 1.2b. Sensor element 1.1, designed using thin-layer technology, is made of a flat metallic basic electrode 1.1c, which is arranged directly on carrier substrate 1.3, and of a moisture-sensitive polymer layer 1.1b arranged thereon. Sensor element 1.1 also includes a moisture-permeable cover electrode 1.1a. Polymer layer 1.1b between the two electrodes 1.1a, 1.1c acts as a dielectric material, and changes its capacitance as a function of the prevailing moisture, and is best used in a generally known fashion for capacitively determining the ambient moisture.

In one example, polyimide can be used as a suitable material for polymer layer 1.1b. For contacting purposes, the two electrodes 1.1a, 1.1c can be connected to the two contacting regions 1.2a, 1.2b, which in turn are further connected to electronic unit 10, as indicated in FIG. 1. A typical thickness of the glass carrier substrate 1.3 can be within the range of about 500–600 μm. The thickness of layers 1.1a, 1.1b, 1.1c arranged thereon can be typically within the range of about 2–3 μm.

This variant of a sensor unit represents only one possible specific embodiment within the present invention. Accordingly, other sensor units for measuring moisture can also be used, where the particular moisture-sensitive sensor element changes another electrical characteristic quantity as a function of moisture. For example, resistive sensor elements could also be used.

In another embodiment, sensor units constructed using thick-layer technology can also be used, as well as sensor units which employ semiconductor materials. As substrate materials, alternatives to glass can also be used. For example, ceramics or silicon can be used.

Thus, within the scope of the present invention, a number of refinements are possible, in addition to the exemplary embodiment described above.

What is claimed is:

1. A device for measuring moisture, comprising:
   a sensor unit with a moisture-sensitive sensor element;
   a carrier element defining a recess, wherein the sensor unit is mounted above the recess, and the moisture-sensitive sensor element is oriented in the direction of the recess;
   first electrical contact regions of the carrier element;
   second electrical contact regions of the sensor unit, the second electrical contact regions being disposed on the sensor unit facing the carrier element; and
   a moisture absorption and desorption resistant coating disposed on the carrier element at least in one partial region adjacent to the sensor unit, wherein the coating is configured to prevent development of a microclimate in an ambient environment of the sensor element to limit erroneous measurements.

2. The device as recited in claim 1, wherein the coating is disposed on substantially the entire surface of the carrier element.

3. The device as recited in claim 1, wherein the coating is made of gold.

4. The device as recited in claim 1, wherein the coating is made of copper.

5. The device as recited in claim 1, wherein the moisture absorption and desorption resistant coating is disposed on edge portions of the carrier element adjacent the recess.

6. The device as recited in claim 1, wherein the moisture absorption and desorption resistant coating is disposed on substantially all edge portions of the carrier element.

7. The device as recited in claim 1, wherein the sensor element has an electrical characteristic property that changes in response to changes in prevailing moisture.

8. The device as recited in claim 1, wherein the carrier element is one of a single-layer and multi-layer circuit board.

9. The device as recited in claim 1, wherein the recess in the carrier element has dimensions that are larger than corresponding dimensions of the sensor unit facing the carrier element.

10. The device as recited in claim 1, further comprising electrically conductive connection elements disposed between the second electrical contact regions of the sensor element and the first electrical contact regions of the carrier element.

11. The device as recited in claim 1, wherein the sensor unit further comprises a carrier substrate on which are disposed a thin-layer sensor element and the second electrical contact regions.

12. The device as recited in claim 11, wherein the thin-layer sensor element further comprises a basic electrode, a polymer layer arranged thereon, and a moisture-permeable cover electrode arranged over the polymer layer.

13. The device as recited in claim 1, further comprising electrical printed conductors disposed on the carrier element, said electrical printed conductors connecting the second electrical contact regions with the first electrical contact regions, wherein the first electrical contact regions are adapted for connection with additional electrical components.

14. The device as recited in claim 13, wherein the printed conductors on the carrier element are formed of the same material forming the coating, said printed conductors being insulated from the coating in selected portions of the carrier element.

15. The device as recited in claim 13, wherein the carrier element is coated with a moisture absorption and desorption resistant solder resist, said solder resist extending over substantially an entire non-contact region surface of the carrier element.

16. A device for measuring moisture, comprising:
    a sensor unit with a moisture-sensitive sensor element;
    a carrier element defining a recess, wherein the sensor unit is mounted above the recess, the moisture-sensitive sensor element is oriented in the direction of the recess;
    electrical contact regions being disposed between the sensor unit and the carrier element to ensure electrical contact with the sensor unit; and
    a moisture absorption and desorption resistant coating disposed on the carrier element at least in one partial region adjacent to the sensor unit.

17. The device as recited in claim 16, wherein the electrical contact regions are applied as soldering paste.

18. The device as recited in claim 16, wherein said electrical contact regions are applied as build-ups composed of electrically conductive solder material.

19. The device as recited in claim 16, wherein said electrical contact regions are applied as build-ups composed of electrically conductive gel material.

20. The device as recited in claim 16, wherein the coating is disposed on substantially the entire surface of the carrier element.

21. The device as recited in claim 16, wherein the coating is made of gold.

22. The device as recited in claim 16, wherein the coating is made of copper.

23. The device as recited in claim 16, wherein the moisture absorption and desorption resistant coating is disposed on edge portions of the carrier element adjacent the recess.

24. The device as recited in claim 16, wherein the moisture absorption and desorption resistant coating is disposed on substantially all edge portions of the carrier element.

25. The device as recited in claim 16, wherein the recess in the carrier element has dimensions that are larger than corresponding dimensions of the sensor unit facing the carrier element.

26. A device for measuring moisture, comprising:
   a sensor unit with a moisture-sensitive sensor element;
   a carrier element defining a recess, wherein the sensor unit is mounted above the recess, and the moisture-sensitive sensor element is oriented in the direction of the recess;
   first electrical contact regions of the carrier element;
   second electrical contact regions of the sensor unit, the second electrical contact regions being disposed on the sensor unit facing the carrier element;
   a moisture absorption and desorption resistant coating disposed on the carrier element at least in one partial region adjacent to the sensor unit; and
   electrical printed conductors disposed on the carrier element, said electrical printed conductors connecting the second electrical contact regions with the first electrical contact regions, wherein the first electrical contact regions are adapted for connection with additional electrical components.

27. The device as recited in claim 26, wherein the coating is disposed on substantially the entire surface of the carrier element.

28. The device as recited in claim 26, wherein the coating is made of gold.

29. The device as recited in claim 26, wherein the coating is made of copper.

30. The device as recited in claim 26, wherein the moisture absorption and desorption resistant coating is disposed on edge portions of the carrier element adjacent the recess.

31. The device as recited in claim 26, wherein the moisture absorption and desorption resistant coating is disposed on substantially all edge portions of the carrier element.

32. The device as recited in claim 26, wherein the printed conductors on the carrier element are formed of the same material forming the coating, said printed conductors being insulated from the coating in selected portions of the carrier element.

33. The device as recited in claim 26, wherein the carrier element is coated with a moisture absorption and desorption resistant solder resist, said solder resist extending over substantially an entire non-contact region surface of the carrier element.

* * * * *